United States Patent [19]

Kadin

[11] Patent Number: 4,678,802
[45] Date of Patent: Jul. 7, 1987

[54] 1-ACYLCARBAMOYLOXINDOLE-3-CAR-BOXAMIDES AS ANTIINFLAMMATORY AGENTS

[75] Inventor: Saul B. Kadin, New London, Conn.

[73] Assignee: Pfizer Inc., New York, N.Y.

[21] Appl. No.: 825,017

[22] Filed: Jan. 31, 1986

Related U.S. Application Data

[63] Continuation-in-part of Ser. No. 753,200, Jul. 9, 1985.

[51] Int. Cl.$^4$ .................... C07D 209/12; A61K 31/40
[52] U.S. Cl. ..................................... 514/418; 548/486
[58] Field of Search ......................... 548/486; 514/418

[56] References Cited

U.S. PATENT DOCUMENTS 3,634,453  1/1972  McManus et al. ................. 548/486
4,556,672  12/1985  Kadin ............................. 514/418 X
4,558,065  12/1985  Urbach et al. ..................... 514/412
4,562,202  12/1985  Urbach et al. ..................... 544/336
4,569,942  2/1986  Kadin ............................. 514/418 X

OTHER PUBLICATIONS

Capuano et al., Chemische Berichte, 105, 2539 (1972).

Primary Examiner—Donald G. Daus
Assistant Examiner—William A. Teoli, Jr.
Attorney, Agent, or Firm—Charles J. Knuth; Peter C. Richardson; J. Trevor Lumb

[57] ABSTRACT

1-Acylcarbamoyloxindole-3-carboxamides as antiinflammatory agents prepared by reaction of the 1-acylcarbamoyloxindole with an isocyanate in the presence of a basic reagent.

8 Claims, No Drawings

1-ACYLCARBAMOYLOXINDOLE-3-CARBOXA-MIDES AS ANTIINFLAMMATORY AGENTS

CROSS REFERENCE TO RELATED APPLICATION

This application is a continuation-in-part of copending application Ser. No. 753,200, filed July 9, 1985.

BACKGROUND OF THE INVENTION

Rheumatoid arthritis, which affects 3-4% of the population, is characterized by inflammation and pain of joints. While the etiology of rheumatoid arthritis is not completely understood, both steroid and non-steroidal antiinflammatory therapy has been used to alleviate the symptoms of this illness. It is to this latter class of non-steroidal antiinflammatory agents that the compounds of the present invention relate.

The potent non-steroidal antiinflammatory agent, piroxicam, 4-hydroxy-2-methyl-N-(2-pyridyl)-2H-1,2-benzothiazine-3-carboxamide 1,1-dioxide was reported in U.S. Pat. No. 3,591,584. More recently, antiinflammatory activity was reported in non-steroidal oxindole-3-carboxamides, U.S. Pat. No. 3,634,453.

SUMMARY OF THE INVENTION

It has now been found that a group of novel 1-acylcarbamoyloxindole-3-carboxamides are useful as analgesic and antiinflammatory agents. More specifically, the novel compounds of the present invention are of the formula

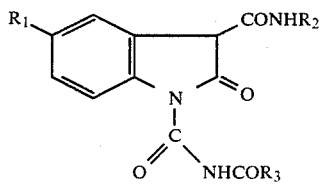

and a pharmaceutically acceptable base salt thereof, wherein $R_1$ is hydrogen, acetyl, methyl, fluoro, chloro, bromo or methoxy; $R_2$ is phenyl or mono- or disubstituted phenyl where said substituent is chloro or fluoro; and $R_3$ is alkyl of one to four carbon atoms or phenyl.

A preferred group of compounds are those where $R_2$ is phenyl or mono- or disubstituted phenyl where said substituent is chloro or fluoro and $R_3$ is phenyl. Especially preferred within this group are the compounds where $R_1$ is acetyl and $R_2$ is 4-chlorophenyl and where $R_1$ is chloro and $R_2$ is phenyl.

A second preferred group of compounds are those where $R_2$ is 2,4-dichlorophenyl and $R_3$ is alkyl of one to four carbon atoms. Especially preferred in this group is the compound where $R_1$ is hydrogen and $R_3$ is t-butyl.

Also included as part of the instant invention is a method of treating an inflammatory disease in a mammalian subject, which comprises administering to said subject an inflammatory disease treating amount of a compound selected from those of the present invention.

In addition, the instant invention comprises a pharmaceutical composition, which comprises a pharmaceutically acceptable carrier and a compound selected from those of the present invention, and wherein the weight-ratio of the pharmaceutically acceptable carrier to said compound is in the range of from 1:4 to 20:1.

DETAILED DESCRIPTION

The process employed in the preparation of the novel compounds of this invention consists of the interaction of an appropriate oxindole derivative with a requisite isocyanate as follows:

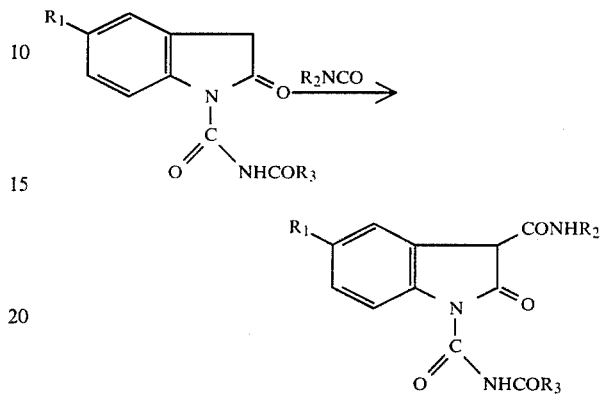

where $R_1$, $R_2$ and $R_3$ are as previously defined.

This reaction leading to the products of the instant invention is carried out in a reaction-inert solvent. Preferred solvents are polar, aprotic solvents such as dimethylformamide, diethylformamide, N-methyl-2-pyrrolidone or dimethylsulfoxide. Further, it is preferred that the reaction be carried out in the presence of a base. Such bases include alkali and alkaline earth metal hydrides or a tertiary organic amine. The preferred base is triethylamine.

In practice, the isocyanate is added to the oxindole derivative and base in the appropriate solvent. It is preferable to employ about a molar equivalent of the isocyanate and two molar equivalents of base, with best results achieved by using an excess of as much as 20% of isocyanate and 100% of base. It is preferred that the reagents be combined in the cold, generally from −5° to 0° C., and that the reaction mixture be allowed to stir at these temperatures for from one to four hours. The reaction can be allowed to warm to room temperature, in which case the reaction is complete in 30–60 minutes.

Upon completion, the reaction can be added to water and acidified to a pH of 2 to 5 using an acid such as hydrochloric acid, or the reaction mixture can be added directly to a 1N solution of hydrochloric acid.

The filtered product can be purified by recrystallization from an appropriate solvent or solvents, or by chromatography.

The oxindole starting reagents for these processes are prepared by methods known to those skilled in the art and by the herein described procedures. The requisite isocyanates are either commercially available or can be prepared by standard procedures known in the art, for instance, Zook and Wagner, Synthetic Organic Chemistry, John Wiley and Sons, Inc., New York, 1956, page 640.

It is noted that a common characteristic of many non-steroidal antiinflammatory agents is their acidic nature. Each of the oxindole carboxamides of the instant invention shares this property and is an effective proton source.

Pharmaceutically acceptable salts of the compounds of the present invention are also therapeutic agents, wherein the preferred cations of said salts include the ammonium, sodium and potassium ions. The pharmaceutically acceptable salts of the compounds described herein are prepared by conventional procedures, as for example, by adding the acid to an aqueous solution containing an equivalent amount of the pharmaceutically acceptable base, i.e., a base containing one of the above preferred cations, followed by concentration of the resultant mixture to obtain the desired product.

The bases can be selected from hydroxides, oxides or carbonates.

As previously indicated, the 1-acylcarbamoyloxindole-3-carboxamides of the present invention and their pharmaceutically acceptable salts are useful antiinflammatory agents. These compounds are of value in alleviating swelling and inflammation which are symptomatic of rheumatoid arthritis and related disorders which are responsive to treatment with antiinflammatory agents. Either as individual therapeutic agents or as mixtures of therapeutic agents, they may be administered alone, but are generally administered with a pharmaceutical carrier selected on the basis of the chosen route of administration and standard pharmaceutical practice. For example, they may be administered orally in the form of tablets or capsules containing such excipients as starch, milk sugar or certain types of clay, etc. They may be administered orally in the form of elixirs or oral suspensions with the active ingredients combined with emulsifying and/or suspending agents. They may be injected parenterally, and for this use they, or appropriate derivatives, may be prepared in the form of sterile aqueous solutions. Such aqueous solutions should be suitably buffered, if necessary, and should contain other solutes such as saline or glucose to render them isotonic. The weight-ratio of the pharmaceutically acceptable carrier to compound can be from 1:4 to 20:1.

The dosage required to reduce inflammation or swelling in arthritic subjects would be determined by the nature and extent of the symptoms. Generally, small doses will be required initially, with a gradual increase in the dose until the optimum level is determined. It will generally be found that when the composition is administered orally, larger amounts of the active ingredient will be required to produce the same level as produced by a smaller quantity administered parenterally. In general, from about 1.0 to about 30 mg of active ingredient per kilogram of body weight, administered orally in single or multiple dose units, will effectively reduce inflammation and swelling. Parenteral administration requires doses of from about 0.5 to about 20 mg per kilogram of active ingredient to achieve the same end point.

A standard procedure for detecting and comparing antiinflammatory activity of compounds is the carrageenin rat foot edema test, which is described by C. A. Winter et al., Proc. Soc. Exp. Biol., vol. III, page 544 (1962).

In addition to being useful as antiinflammatory agents, the compounds of the present invention can be used in the treatment of asthma, bronchitis and psoriasis; they can also be used as analgesic agents.

The following examples are provided solely for the purpose of further illustration.

EXAMPLE 1

1-(N-benzoylcarbamoyl)-3-(4-chlorophenylcarboxamido)-5-acetyloxindole($R_1 = CH_3CO$; $R_2 = $ 4-chlorophenyl; and $R_3 = $ phenyl)

To 1.0 g (0.0031 mole) of 1-(N-benzoylcarbamoyl)-5-acetyloxindole in 40 ml of dimethylformamide was added 1.1 ml (0.0079 mole) of triethylamine and the solution cooled to 0°–5° C. To the cold reaction mixture was added 610 mg (0.00397 mole) of 4-chlorophenylisocyanate and the reaction stirred for 2 hours. The reaction was added to 300 ml of 1N hydrochloric acid and allowed to stir for 30 minutes. The product was filtered, washed with water (2×25 ml) and dried, 940 mg m.p. 213° C. dec.

Calc'd for $C_{25}H_{18}O_5N_3Cl$:
C, 63.1; H, 3.8; N, 8.8.
Found: C, 63.2; H, 3.8; N, 8.9.

EXAMPLE 2

Employing the procedure of Example 1 and starting with the appropriate isocyanate and requisite 1-acylcarbamoyloxindole, the following products are prepared:

1-(N-acetylcarbamoyl)-3-phenylcarboxamido-5-acetyloxindole; 1-(N-s-butyrylcarbamoyl)-3-(3,5-dichlorophenylcarboxamido)-5-acetyloxindole; 1-(N-pivaloylcarbamoyl)-3-(2,4-difluorophenylcarboxamido)-5-acetyloxindole; 1-(N-acetylcarbamoyl)-3-(4-fluorophenylcarboxamido)-5-acetyloxindole; 1-(N-acetylcarbamoyl)-3-(2-chlorophenylcarboxamido)-5-acetyloxindole; 1-(N-propionylcarbamoyl)-3-(2-fluoro-3-chlorophenylcarboxamido)-5-acetyloxindole; and 1-(N-pivaloylcarbamoyl)-3-(4-fluorophenylcarboxamido)-5-acetyloxindole.

EXAMPLE 3

1-(N-Benzoylcarbamoyl)-3-phenylcarboxamido-5-chlorooxindole ($R_1 = $ chloro; $R_2 = $ phenyl; and $R_3 = $ phenyl)

To a solution of 1.0 g (0.0032 mole) of 1-(N-benzoylcarbamoyl)-5-chlorooxindole in 25 ml of dimethylformamide cooled to 0°–5° C. was added 0.77 ml (0.0076 mole) of triethylamine followed by 0.42 ml (0.0038 mole) of phenylisocyanate. After stirring for 2 hours at 0.5° C. the reaction mixture was poured into 300 ml of cold 1N hydrochloric acid and the resulting mixture stirred for 30 minutes. The product was filtered, washed with water (2×25 ml) and air dried. The product was purified by recrystallization from methanolacetonitrile (1:10; v:v), 800 mg, m.p. 208° C. dec. Anal. Calc'd for $C_{23}H_{16}O_4N_3Cl$:
C, 63.7; H, 3.7; N, 9.7.
Found C, 64.0; H, 3.8; N, 9.7.

EXAMPLE 4

Following the procedure of Example 3 and starting with the appropriate reagents, the indicated products are prepared:

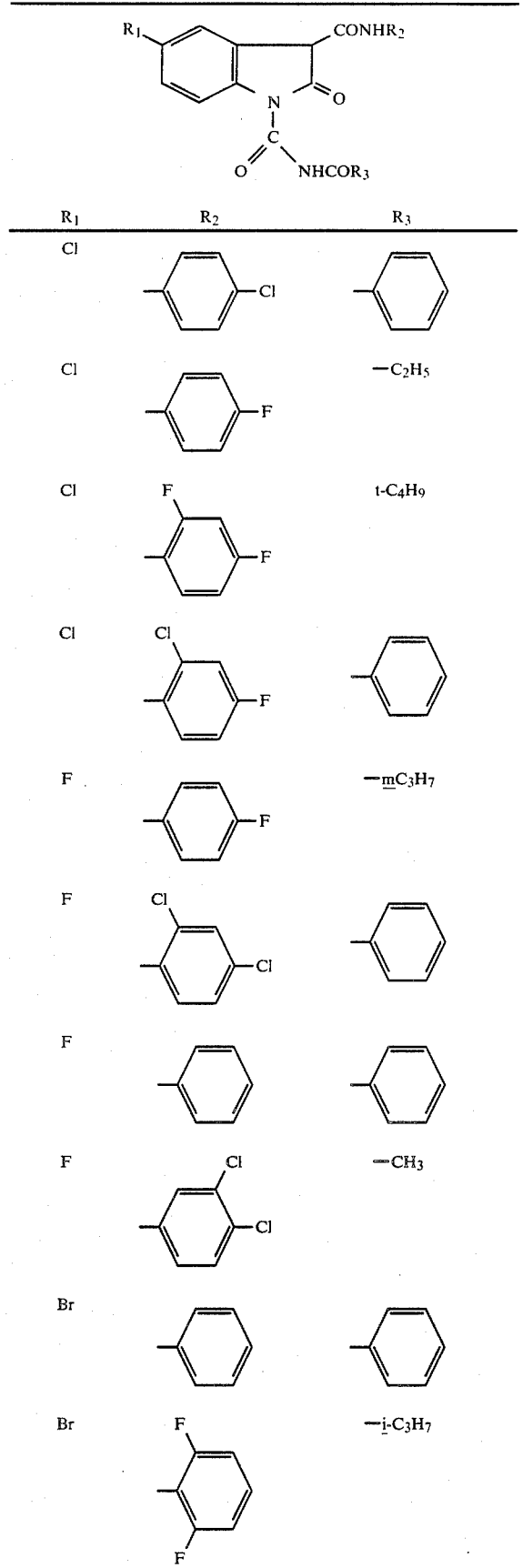

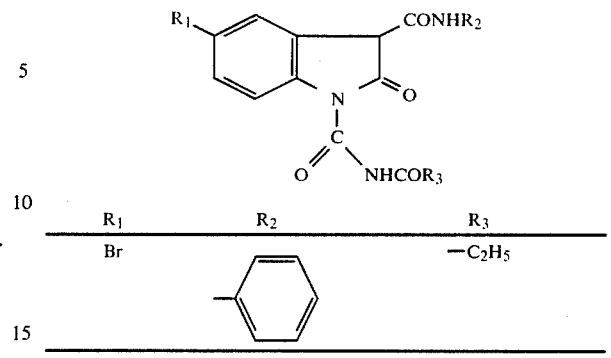

EXAMPLE 5

1-(N-Pivaloylcarbamoyl)-3-(2,4-dichlorophenylcarboxamido)oxindole ($R_1$=H; $R_2$=2,4-dichlorophenyl; and $R_3$=t-$C_4H_9$)

To a solution of 1.0 g (0.0038 mole) of 1-(N-pivaloylcarbamoyl)oxindole in 25 ml of dimethylformamide was added 1.3 ml (0.0092 mole) of triethylamine followed by 870 mg (0.0046 mole) of 2,4-dichlorophenylisocyanate, and the reaction mixture stirred at 0.5° C for 2 hours. The mixture was poured into 300 ml of cold 1N hydrochloric acid, and the solids extracted with 75 ml of chloroform. The organic phase was dried and the product precipitated by the addition of an equal volume of hexane. The solids were filtered and dried, 300 mg, m.p. 176° C. dec.

Anal Calc'd for $C_{21}H_{19}O_4N_3Cl_2$:
C, 56.3; H, 4.3; N, 9.4.
Found :C, 56.5; H, 4.2; N, 9.4.

EXAMPLE 6

The procedure of Example 5 was repeated, starting with the appropriate reagents, to give the following compounds:

1-(N-benzoylcarbamoyl)-3-(2,4-difluorophenylcarboxamido)-5-methyloxindole; 1-(N-acetylcarbamoyl)-3-(phenylcarboxamido)-5-methyloxindole; 1-(N-pivaloylcarbamoyl)-3-(4-fluorophenylcarbamoyl)-5-methyloxindole; 1-(N-benzoylcarbamoyl)-3-(3,4-dichlorophenylcarboxamido)-5-methyloxindole; 1-(N-propionylcarbamoyl)-3-(2-fluoro-4-chlorophenylcarboxamido)-5-methyloxindole; 1-(N-butyrylcarbamoyl)-3-(2,4-dichlorophenylcarboxamido)-5-methoxyoxindole; 1-(N-benzoylcarbamoyl-3-(2,4-difluorophenylcarboxamido)-5-methoxyoxindole; 1-(N-acetylcarbamoyl)-3-(phenylcarboxamido)-5-methoxyoxindole; and 1-(N-pivaloylcarbamoyl)-3-(4-chlorophenylcarboxamido)-5-methoxyoxindole.

PREPARATION A

1-(N-Benzoylcarbamoyl)-5-acetyloxindole

To 3.0 g (0.017 mole) of 5-acetyloxindole in 75 ml of xylene and 25 ml of toluene was added 3.3 g (0.022 mole) of benzoylisocyanate, and the reaction mixture heated to reflux overnight. The hot suspension was filtered, washed with toluene and air dried, 4.4 g, m.p. 232° C. dec.

In a similar manner 1-(N-acetylcarbamoyl)-5-acetyloxindole, 1-(N-s-butyrylcarbamoyl)-5-acetyloxindole, 1-(N-pivaloylcarbamoyl)-5-acetyloxindole and 1-(N-propionylcarbamoyl)-5-acetyloxindole are prepared.

PREPARATION B

1-(N-Benzoylcarbamoyl)-5-chlorooxindole

Benzoylisocyanate (6.4 g, 0.043 mole) was added to 6 g (0.036 mole) of 5-chlorooxindole in 150 ml of toluene, and the reaction mixture heated to reflux for 7 hours. The mixture was cooled and the product filtered and washed with toluene. Recrystallization from acetonitrile gave 4 g of product, m.p. 198°–200° C.

Using a similar procedure, 1-(N-propionylcarbamoyl)-5-chlorooxindole, 1-(N-pivaloylcarbamoyl)-5-chlorooxindole, 1-(N-butyrylcarbamoyl)-5-fluorooxindole, 1-(N-benzoyl-carbamoyl)-5-fluorooxindole, 1-(N-acetylcarbamoyl)-5-fluorooxindole, 1-(N-benzoylcarbamoyl)-5-bromooxindole, 1-(N-i-butyrylcarbamoyl)-5-bromooxindole and 1-(N-propionylcarbamoyl)-5-bromooxindole are prepared.

PREPARATION C

1-(N-Pivaloylcarbamoyl)oxindole

To a solution of 2.5 g (0.0188 mole) of oxindole in 150 ml of toluene was added 3.1 g (0.024 mole) of pivaloylisocyanate and the resulting reaction mixture heated to reflux. Each hour an additional 3.1 g of isocyanate was added until a total of about 12 g was added. The reaction was heated to reflux overnight and the volume concentration in vacuo to about one-fourth. The solids were filtered and recrystallized from methanol, 3.1 g, m.p. 154°–155° C.

Employing the above procedure, 1-(N-benzoylcarbamoyl)-5-methyloxindole, 1-(N-acetylcarbamoyl)-5-methyloxindole, 1-(N-pivaloylcarbamoyl)-5-methyloxindole, 1-(N-propionylcarbamoyl)-5-methyloxindole, 1-(N-butyrylcarbamoyl)-5-methoxyoxindole, 1-(N-benzoylcarbamoyl)-5-methoxyoxindole and 1-(N-acetylcarbamoyl)-5-methoxyoxindole are prepared.

PREPARATION D

5-Chlorooxindole

To a stirred slurry of 100 g (0.55 mol) of 5-chloroisatin in 930 ml of ethanol was added 40 ml (0.826 mol) of hydrazine hydrate, resulting in a red solution. The solution was heated under reflux for 3.5 hours, during which time a precipitate appeared. The reaction mixture was stirred overnight, and then the precipitate was recovered by filtration to give 5-chloro-3-hydrazonooxindole as a yellow solid, which was dried in a vacuum oven. The dried solid weighted 105.4 g.

The dried solid was then added portionwise, during 10 minutes, to a solution of 125.1 g of sodium methoxide in 900 ml of absolute ethanol. The resultant solution was heated under reflux for 10 minutes and then it was concentrated in vacuo to a gummy solid. The gummy solid was dissolved in 400 ml of water and the aqueous solution thus obtained was decolorized with activated carbon and then poured into a mixture of 1 liter of water and 180 ml of concentrated hydrochloric acid containing ice chips. A tan solid precipitated and it was cooled by filtration and washed thoroughly with water. The solid was dried and then it was washed with diethyl ether. Finally it was recrystallized from ethanol to give 48.9 g of the title compound, m.p. 193°–195° C. dec.

In a similar manner 5-methylisatin is converted to the corresponding methyloxindole.

PREPARATION E

5-Fluorooxindole

To a stirred solution of 11.1 g (0.1 mol) of 4-fluoroaniline in 200 ml of dichloromethane, at −60° to −65° C., was added, dropwise, a solution of 10.8 g (0.1 mol) of t-butyl hypochlorite in 25 ml of dichloromethane. Stirring was continued for 10 minutes at −60° to −65° C., and then was added, dropwise, a solution of 13.4 g (0.1 mol) of ethyl 2-(methylthio)acetate in 25 ml of dichloromethane. Stirring was continued at −60° C. for 1 hour and then was added, dropwise, at −60° C. to −65° C., a solution of 11.1 g (0.11 mol) of triethylamine in 25 ml of dichloromethane. The cooling bath was removed, and when the reaction mixture had warmed to room temperature, 100 ml of water was added. The phases were separated, and the organic phase was washed with saturated sodium chloride solution, dried ($Na_2SO_4$) and evaporated in vacuo. The residue was dissolved in 350 ml of diethyl ether, to which was added 40 ml of 2N hydrochloric acid. This mixture was stirred at room temperature overnight. The phases were separated and the ether phase was washed with water, followed saturated sodium chloride. The dried ($Na_2SO_4$) ether phase was evaporated in vacuo to give 17 g of an orange-brown solid which was triturated under isopropyl ether. The solid was then recrystallized from ethanol, to give 5.58 g of 5-fluoro-3-methylthiooxindole, m.p. 151.5°–152.5° C.

Anal. Calc'd. for $C_9H_8ONFS$:
C, 54.80; H, 4.09; N, 7.10%.
Found: C, 54.74; H, 4.11; N, 7.11%.

A sample of the above 5-fluoro-3-methylthiooxindole (986 mg 5.0 mmole) was added to 2 teaspoonsful of Raney nickel under 50 ml of absolute ethanol, and then the reaction mixture was heated under reflux for 2 hours. The catalyst was removed by decantation and was washed with absolute ethanol. The combined ethanol solutions were evaporated in vacuo and the residue was dissolved in dichloromethane. The dichloromethane solution was dried ($Na_2SO_4$) and evaporated in vacuo to give 475 mg of 5-fluorooxindole, m.p. 121°–134° C.

PREPARATION F

5-Methoxyoxindole

5-Methoxyoxindole was prepared from 4-methoxyaniline in a manner similar to the procedure of Preparation E, except that the initial chlorination step was carried out using a solution of chlorine gas in dichloromethane in place of t-butyl hypochlorite. The title product melted at 150.5°–151.5° C.

PREPARATION G

5-Bromooxindole

5-Bromooxindole was prepared according to the procedure described by Beckett et al., Tetrahedron, 24, 6093 (1968), as was 5-methoxyoxindole.

PREPARATION H

5-Acetyloxindole

The titled compound was prepared by reaction of oxindole with acetyl chloride and aluminum chloride in carbon disulfide.

I claim:
1. A compound of the formula

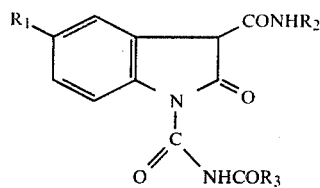

and a pharmaceutically acceptable base salt thereof, wherein $R_1$ is selected from the group consisting of hydrogen, acetyl, methyl, fluoro, chloro, bromo and methoxy; $R_2$ is selected from the group consisting of phenyl and mono- and disubstituted phenyl wherein said substituents are selected from the group consisting of chloro and fluoro; and $R_3$ is selected from the group consisting of alkyl having one to four carbon atoms and phenyl.

2. A compound of claim 1, wherein $R_2$ is selected from the group consisting of phenyl and mono- and disubstituted phenyl wherein said substituent is selected from the group consisting of chloro and fluoro; and $R_3$ is phenyl.

3. The compound of claim 2, wherein $R_1$ is acetyl and $R_2$ is 4-chlorophenyl.

4. The compound of claim 2, wherein $R_1$ is chloro and $R_2$ is phenyl.

5. A compound of claim 1, wherein $R_2$ is 2,4-dichlorophenyl and $R_3$ is alkyl having one to four carbon atoms.

6. The compound of claim 5, wherein $R_1$ is hydrogen and $R_3$ is t-butyl.

7. A method of treating an inflammatory disease in a mammalian subject, which comprises administering to said mammalian subject an inflammatory disease treating amount of a compound selected from claim 1.

8. An antiflammatory composition, which comprises a pharmaceutically acceptable carrier and an effective antiflammatory amount of a compound selected from claim 1, and wherein the weight-ratio of the pharmaceutically acceptable carrier to said compound is in the range of from 1:4 to 20:1.

* * * * *